United States Patent [19]

Wright et al.

[11] 4,169,097

[45] Sep. 25, 1979

[54] 2,3-DIHYDRO-4H-1-BENZOPYRAN-4-ONE O-CARBAMOYL OXIMES

[75] Inventors: George C. Wright; Thomas J. Schwan; Marvin M. Goldenberg, all of Norwich, N.Y.

[73] Assignee: Morton-Norwich Products, Inc., Norwich, N.Y.

[21] Appl. No.: 892,824

[22] Filed: Apr. 3, 1978

[51] Int. Cl.² .................................. C07D 311/02
[52] U.S. Cl. .......................... 260/345.2; 260/345.5; 424/283

[58] Field of Search .................. 260/345.2, 345.5

[56] References Cited

U.S. PATENT DOCUMENTS 4,065,574  12/1977  Moon et al. .................. 260/345.2

*Primary Examiner*—Nicky Chan
*Attorney, Agent, or Firm*—Anthony J. Franze

[57] ABSTRACT

A series of 2,3-dihydro-4H-1-benzopyran-4-one O-carbamoyl-oximes are useful as gastric antisecretory agents.

10 Claims, No Drawings

2,3-DIHYDRO-4H-1-BENZOPYRAN-4-ONE O-CARBAMOYL OXIMES

This invention is concerned with chemical compounds and particularly with a series of 2,3-dihydro-4H-1-benzopyran-4-one O-carbamyloximes of the formula:

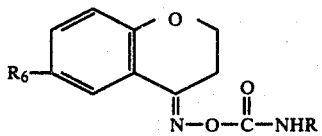

wherein R is hydrogen, lower alkyl of 1–3 carbon atoms, or propenyl and $R_6$ is hydrogen, chloro, methoxy or amino. The members of this series are useful as gastric antisecretory agents.

The compounds of this invention are readily prepared by bringing together the appropriate 2,3-dihydro-4H-1-benzopyran-4-one oxime (4-chromanone oxime) and appropriate isocyanate in the presence of a solvent inert to the reactants. The following examples illustrate the method currently preferred for the preparation of the compounds of this invention:

EXAMPLE I

2,3-Dihydro-4H-1-benzopyran-4-one O-(Methylcarbamoyl) oxime

A 60 g (0.37 mole) portion of 4-chromanone oxime in 770 ml of benzene was refluxed until all water was removed via a Dean-Stark trap, 0.5 hrs. The solution was cooled to 25°–30°, treated with 0.5 ml of triethylamine followed by the dropwise addition of 20 ml (0.33 mole) of methyl isocyanate at less than 70°. The reaction mixture was refluxed for 3 hrs., stored at room temperature overnight, filtered, and stripped of benzene under reduced pressure. The residue was treated with 200 ml of ether, cooled 20 min. and filtered. The white crystalline product was washed with 100 ml of ether and dried, m.p. 123°–126°. Yield: 64 g (88%).

The product was recrystallized from 279 ml of isopropanol, washed with 50 ml of isopropanol, ether and dried, m.p. 125°–126°. Yield: 56 g (81%).

Anal. Calc'd. for $C_{11}H_{12}N_2O_3$: C, 59.99; H, 5.49; N, 12.72. Found: C, 59.76; H, 5.59; N, 12.69.

EXAMPLE II

2,3-Dihydro-6-methoxy-4-H-1-benzopyran-4-one O-(Ethylcarbamoyl)-oxime

A 42 g (0.22 mole) portion of 6-methoxy-4-chromanone oxime in 600 ml of benzene was refluxed until all water was removed via a Dean-Stark trap. The solution was treated with 1 ml of triethylamine, followed by the dropwise addition of 14 g (0.20 mole) of ethyl isocyanate at reflux. The reaction mixture was refluxed for 4 hrs., stored overnight at room temperature, and stripped of benzene under reduced pressure. The viscous residue was taken up in 250 ml of ether, refrigerated 6 hrs., and filtered. The cream colored solid was washed with 150 ml of ether and dried, m.p. 97°–98°. Yield: 44 g (83%).

The product was recrystallized from 150 ml of isopropanol, washed with isopropanol, ether, m.p. 97°–98°. Yield: 39 g (74%).

Anal. Calc'd. for $C_{13}H_{16}N_2O_4$: C, 59.08; H, 6.10; N, 10.60. Found: C, 59.21; H, 6.16; N, 10.56.

EXAMPLE III

2,3-Dihydro-4-H-1-Benzopyran-4-one O-(Ethylaminocarbonyl)oxime

4-Chromanone oxime (20 g, 0.12 mole) was added to benzene (260 ml) and refluxed for 45 min. in a flask equipped with a Dean-Stark trap. The solution was cooled to 25°–30°, triethylamine (0.5 ml) was added, followed by ethyl isocyanate (8.5 g, 0.12 mole). The solution was refluxed for 3 hrs. and stored overnight at room temperature. The mixture was filtered and the filtrate was stripped of solvent under reduced pressure. Anhydrous ether (100 ml) was added to the residue and the mixture was cooled for 3 hrs. The product was collected by filtration, yield: 20 g (79%). A sample was recrystallized from isopropanol, m.p. 110°–111°.

Anal. Calc'd. for $C_{12}H_{14}N_2O_3$: C, 61.53; H, 6.02; N, 11.96. Found: C, 61.44; H, 5.92; N, 11.98.

EXAMPLE IV

2,3-Dihydro-6-methoxy-4H-1-benzopyran-4-one O-(Methylaminocarbonyl)oxime

10% NaOH (200 ml) was added to a rapidly stirring solution of hydroxylamino hydrochloride (50 g, 0.72 mole) in $H_2O$ (225 ml). A solution of 6-methoxy-4-chromanone (36 g, 0.20 mole) in ethanol (325 ml) was added and the mixture was heated on the steam bath for 15 min. with the temperature rising to 82°. The steam bath was removed and the mixture was stirred for 3 hrs., then cooled overnight. The product was collected by filtration and air-dried, yield: 37 g (96%).

6-Methoxychromanone oxime (37 g, 0.19 mole) was added to benzene (400 ml) and the mixture was refluxed for 45 minutes in a flask equipped with a Dean-Stark trap. The heat was removed and triethylamine was added at 27°; followed by methyl isocyanate (12 g, 0.21 mole). The mixture was refluxed for 3 hrs. and stored overnight at room temperature. The mixture was stripped of solvent, the residue washed in anhydrous ether, and the product was collected by filtration. The product was recrystallized twice from isopropanol, m.p. 119°–120°, yield: 28 g (59%).

Anal. Calc'd. for $C_{12}H_{14}N_2O_4$: C, 57.59; H, 5.64; N, 11.20 Found: C, 57.55; H, 5.66; N, 11.20.

EXAMPLE V

6-Chloro-2,3-dihydro-4H-1-benzopyran-4-one O-(Methylaminocarbonyl)oxime

10% NaOH (90 ml) was added to a rapidly stirring solution of hydroxylamino hydrochloride (22 g, 0.32 mole) in $H_2O$ (100 ml). 6-Chloro-4-chromanone (17 g, 0.09 mole) was added to absolute ethanol (185 ml) and heated. The solution was added to the reaction and the resulting mixture was heated to 82° in 15 min. The heat was removed and the mixture was stirred for 3 hrs. The mixture was cooled overnight and the product collected by filtration, yield: 6 g. The filtrate was concentrated to 40 ml under reduced pressure. The solution was cooled and the resultant product was collected by filtration, then combined with the previous product, total yield: 9.7 g (55%).

6-Chloro-4-chromaone oxime (9.7 g, 0.049 mole) was added to benzene (125 ml) and the mixture was refluxed for 45 min. in a flask equipped with a Dean-Stark trap.

The solution was cooled to room temperature and triethylamine (0.5 ml) was added, followed by methyl isocyanate (3.1 g, 0.054 mole). The mixture was refluxed for 3 hrs. and stored overnight at room temperature. The product was collected by filtration, yield: 10 g (80%). A sample was recrystallized from benzene, m.p. 182°–184°.

Anal. Calc'd. for $C_{11}H_{11}ClN_2O_3$: C, 51.68; H, 4.35; N, 11.00. Found: C, 51.50; H, 4.23; N, 10.80.

EXAMPLE VI

6-Amino-2,3-dihydro-4H-1-benzopyran-4-one O(Methylaminocarbonyl)oxime

Sodium methoxide (10 g, 0.18 mole) was added to a solution of hydroxylamine hydrochloride (14 g, 0.20 mole) in absolute alcohol (400 ml). The mixture was stirred for 3 min., filtered and filtrate was added to 6-nitro-4-chromanone (21 g, 0.11 mole). The mixture was refluxed for 4 hrs. and the resultant solution was concentrated to 150 ml under reduced pressure and cooled overnight. The product was collected by filtration, yield: 15 g. The filtrate was diluted with water (300 ml) and the product was collected by filtration, total yield: 19 g (83%).

A mixture of 6-nitro-4-chromanone oxime (19 g, 0.09 mole) and benzene (200 ml) was refluxed for 45 min. in a flask equipped with a Dean-Stark trap. The heat was removed and triethylamine (0.5 ml) was added, followed by methyl isocyanate (7.3 g, 0.10 mole) in benzene (30 ml). The mixture was refluxed for 3 hrs. and stored overthe weekend at room temperature. The product was collected by filtration, stirred in hot absolute alcohol (150 ml) and cooled overnight. The product was collected by filtration, yield: 16 g (67%). A sample was recrystallized from absolute alcohol, m.p. 204°–207°.

Anal. Calc'd. for $C_{11}H_{11}N_3O_5$: C, 49.81; H, 4.18; N, 15.85. Found: C, 49.80; H, 4.24; N, 15.65.

A mixture of 6-nitro-4H-1-benzopyran-4-one O-(methylaminocarbonyl)oxime (4 g, 0.016 mole), $PtO_2$ (0.2 g) and absolute alcohol (200 ml) was subjected to hydrogenation at room temperature for 21 hrs. using 53 psia $H_2$ (theory: 48 psia $H_2$). The catalyst was removed by filtration, the filtrate cooled in an ice bath, and the solution adjusted to pH 3 with ethanol/HCl. The solution was concentrated to 70 ml under reduced pressure, cooled, and the product collected by filtration, yield: 2.5 g (58%).

A sample was recrystallized from methanol, m.p. 194°–199°.

Anal. Calc'd. for $C_{11}H_{13}N_3O_3 \cdot HCl$: C, 48.62; H, 5.19; N, 15.47. Found: C, 48.46; H, 5.18; N, 15.13.

EXAMPLE VII 2,3-Dihydro-4H-1-benzopyran-4-one O-[(2-Propenyl)aminocarbonyl]oxime A solution containing 6.52 g (0.04 mole) of 4-chromanone oxime and 75 ml benzene was stirred and refluxed for 0.50 hrs. using a Dean-Stark apparatus. The solution was cooled to 60° and 6 drops triethylamine and 3.32 g (0.04 mole) allyl isocyanate in 10 ml benzene was added. The solution was stirred and refluxed for 4 hrs., concentrated to dryness, and the residue was recrystallized from 20 ml toluene to give 7.15 g (73%) of the product, m.p. 83°–86°.

Anal. Calc'd. for $C_{13}H_{14}N_2O_3$: C, 63.40; H, 5.73; N, 11.38. Found: C, 63.38; H, 5.81; N, 11.40.

EXAMPLE VIII 2,3-Dihydro-4H-1-benzopyran-4-one O-(1-Propylaminocarbonyl)oxime A solution of 6.62 g (0.04 mole) of 4-chromanone oxime and 75 ml toluene was stirred and refluxed for 0.50 hrs. using a Dean-Stark apparatus. The solution was cooled at 50° and 6 drops triethylamine and 3.40 g (0.04 mole) of n-propyl isocyanate in 25 ml toluene was added. The solution was concentrated to dryness and the residue was recyrstallized from 10 ml of toluene to give 6.70 g (68%) of the product, m.p. 79.5°–81.5°.

Further recrystallization frm toluene gave an analytical sample, m.p. 79.5°–81.0°.

Anal. Calc'd. for $C_{13}H_{16}N_2O_3$: C, 62.89; H, 6.50; N, 11.28. Found: C, 62.78; H, 6.67; N, 10.96.

EXAMPLE IX 2,3-Dihydro-4H-1-benzopyran-4-one O-(Aminocarbonyl)oxime

To a solution of 8.15 g (0.05 mole) of 4-chromanone oxime in 175 ml glacial acetic acid at room temperature was added a solution of 4.05 g (0.05 mole) potassium cyanate in 20 ml water. The solution was stirred at ambient temperature for 48 hrs., diluted with 200 ml water, and extracted with 2×150 ml chloroform. The combined extracts were dried over magnesium sulfate, concentrated to dryness in vacuo, and the residue was recrystallized from 40 ml of toluene to give 4.58 g (44%) of the product, m.p. 118°–127°.

An analytical sample, m.p. 120°–122°, was obtained by recrystallization from toluene.

Anal. Calc'd. for $C_{10}H_{10}N_2O_3$: C, 58.25; H, 4.89; N, 13.58. Found: C, 58.59; H, 4.77; N, 13.45.

The compounds of this invention exhibit a salutary effect upon gastric acid secretion. Such effect is evidenced using a modified standard pylorus-ligated secretory testing procedure in the rat. Sprague-Dawley rats, weighing 180–210 g and previously fasted for 24 hrs., were used. All compounds were given perorally as suspensions in 0.5% Methocel 1 hr. prior to pylorus ligation. Under light ether anesthesia, the rat stomach was ligated at the pylorus region. Four hrs. after ligation, the conscious rat was sacrificed by a chloroform overdose. The stomach was carefully excised and its content drained into a centrifuge tube. Samples were centrifuged to separate secretions from debris. Gastric fluid volume reading and determination of sample contamination, based on debris and sample color, was made. Titration was performed on a sample aliquot from 1 ml diluted to a volume of 5 ml using distilled water. The titrant used was 0.1 N NaOH. Total gastric acid output in the stomach was determined by titration to pH 7. A dose from 50–100 mg/kg p.o. of a compound was administered to a group of rats and its effect on the volume of gastric secretion and acid output compared to a control group receiving 0.5% Methocel p.o. The activity of each compound based on the degree of inhibition of gastric acid output is set forth in Table I.

Table I

| Compound of Example | % Inhibition | |
|---|---|---|
| | Gastric acid output | Volume of gastric secretion |
| I | 60.4 | 34.1 |
| II | 57.7 | 33.2 |
| III | 79.7 | 61.8 |
| IV | 45.5 | 35.3 |

Table I-continued

| Compound of Example | % Inhibition | |
|---|---|---|
| | Gastric acid output | Volume of gastric secretion |
| V | 40.0 | 55.2 |
| VI | 55.8 | 64.4 |
| VII | 89.9 | 76.2 |
| VIII | 88.1 | 73.1 |
| IX | 77.9 | 60.5 |

The compounds of this invention are readily combined in classical dosage unit forms such as tablets, elixirs, solutions, capsules, suspensions and the like using conventional excipients and adjuvants with which there is no incompatibility.

What is claimed is:

1. A compound of the formula:

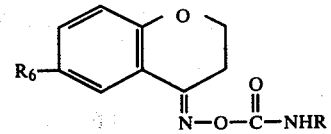

wherein R is a hydrogen, lower alkyl of 1–3 carbon atoms or 2-propenyl and $R_6$ is hydrogen, chloro, methoxy, or amino.

2. The compound 2,3-dihydro-4H-1-benzopyran-4-one O-(methylaminocarbonyl)oxime.

3. The compound 2,3-dihydro-6-methoxy-4H-1-benzopyran-4-one O-(ethylaminocarbonyl)oxime.

4. The compound 2,3-dihydro-4H-1-benzopyran-4-one O-(ethylaminocarbonyl)oxime.

5. The compound 2,3-dihydro-6-methoxy-4H-1-benzopyran-4-one O-(methylaminocarbonyl)oxime.

6. The compound 6-chloro-2,3-dihydro-4H-1-benzopyran-4-one O-(methylaminocarbonyl)oxime.

7. The compound 6-amino-2,3-dihydro-4H-1-benzopyran-4-one O-(methylaminocarbonyl)oxime.

8. The compound 2,3-dihydro-4H-1-benzopyran-4-one O-[(2-propenyl)aminocarbonyl]oxime.

9. The compound 2,3-dihydro-4H-1-benzopyran-4-one O-[(1-propyl)aminocarbonyl]oxime.

10. The compound 2,3-dihydro-4H-1-benzopyran-4-one O-(aminocarbonyl)oxime.

* * * * *